US006222069B1

(12) United States Patent
Henriet et al.

(10) Patent No.: US 6,222,069 B1
(45) Date of Patent: Apr. 24, 2001

(54) METHOD FOR PURIFYING ADIPIC ACID IN WATER

(75) Inventors: Eric B. Henriet, Lyons; Philippe Leconte, Meyzieu; Carl Patois, Lyons; Robert Perron, Charly, all of (FR)

(73) Assignee: Rhodia Fiber and Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/194,924

(22) PCT Filed: May 29, 1997

(86) PCT No.: PCT/FR97/00938

§ 371 Date: Mar. 17, 1999

§ 102(e) Date: Mar. 17, 1999

(87) PCT Pub. No.: WO97/46509

PCT Pub. Date: Dec. 11, 1997

(30) Foreign Application Priority Data

Jun. 4, 1996 (FR) .................................................. 9607170

(51) Int. Cl.[7] ............................ C07C 55/00; C07C 51/00
(52) U.S. Cl. ......................... 562/590; 562/513; 562/522; 562/591; 562/593
(58) Field of Search ..................................... 562/522, 591, 562/513, 593, 590

(56) References Cited

U.S. PATENT DOCUMENTS

| 5,166,421 | * | 11/1992 | Bruner, Jr. ............................ 562/522 |
| 5,264,624 | * | 11/1993 | Vogtel et al. ........................ 562/513 |
| 5,587,511 | * | 12/1996 | Salzburg et al. ..................... 562/513 |
| 6,008,408 | * | 12/1998 | Denis et al. ......................... 562/517 |

FOREIGN PATENT DOCUMENTS

| 737 691 | 7/1943 | (DE) . |
| 0 502 384 | 9/1992 | (EP) . |
| 0 712 830 | 5/1996 | (EP) . |
| 901 841 | 8/1945 | (FR) . |

* cited by examiner

*Primary Examiner*—Porfirio Nazario-Gonzalez
(74) *Attorney, Agent, or Firm*—Burns, Doane, Swecker & Mathis, L.L.P.

(57) ABSTRACT

The invention discloses a method for purifying adipic acid in water. More precisely it discloses an improvement in adipic acid crystallization or recrystallization in water, characterised in that the said crystallization or recrystallization is effected in presence of a strong proton acid and/or in the presence of carbon monoxide. This crystallization or recrystallization particularly enables the content of metal catalyst traces in the adipic acid to be reduced.

10 Claims, No Drawings

METHOD FOR PURIFYING ADIPIC ACID IN WATER

The present invention relates to a process for purifying adipic acid in water.

Adipic acid is one of the two base materials for preparing polyamide 6—6. For the applications of polyamide 6—6 it is necessary to have a very high purity, and this purity must exist already at the stage of the precursors, especially at the adipic acid stage.

Depending on the process by which adipic acid is prepared the impurities it contains are obviously different. The present process can be applied to adipic acid originating from various processes of synthesis. In fact, one of the most troublesome and sometimes most costly impurities is formed by the presence of traces of the catalyst employed during the preparation of adipic acid.

However, in the description which follows, the process will be applied more particularly to adipic acid obtained from the double hydroxycarbonylation of butadiene or from the oxidation of cyclohexane.

The first hydroxycarbonylation of butadiene leads to a mixture of pentenoic acids, principally 3-pentenoic acid. The second hydroxycarbonylation affects the pentenoic acids obtained in the first reaction and leads to adipic acid which also includes a certain amount of 2-methylglutaric acid, 2-ethylsuccinic acid and other compounds originating from the first hydroxycarbonylation reaction, such as gamma-valerolactone, unconverted pentenoic acids, and methylbutenoic acid. It also includes traces of the catalyst employed in the second hydroxycarbonylation reaction, usually iridium and/or rhodium.

The direct oxidation of cyclohexane to adipic acid is generally carried out in the presence of cobalt, and in this process the adipic acid obtained contains traces of cobalt catalyst.

Since adipic acid is of low solubility in water when cold but is much more soluble when hot, this solvent is generally employed for the crystallization of the said acid.

However, owing to the very high purities which are increasingly required for adipic acid, especially insofar as trace metals are concerned, one or even a number of recrystallizations from water often prove to be inadequate.

Besides the trouble which can be caused by the presence of trace metals to the various uses of adipic acid, the intrinsic value of certain catalysts, such as iridium or rhodium, bearing in mind the very large tonnages of adipic acid, means that it is essential to recover them as thoroughly as possible in the context of an economically viable industrial process.

The present invention consists in an improved process for crystallization or recrystallization of adipic acid in water, characterized in that the said crystallization or recrystallization is carried out in the presence of a strong protic acid and/or in the presence of carbon monoxide.

In this text strong protic acid is understood to mean an inorganic protic acid which has a pKa of less than 1.

As nonlimitative examples of such strong protic acids mention may be made of hydroiodic acid, hydrobromic acid, hydrochloric acid, nitric acid and sulphuric acid.

The quantity of strong protic acid can vary from 0 to 100 mol per mole of catalyst metal present in the adipic acid. Preferably, the quantity of protic acid varies from 1 to 50 mol per mole of catalyst metal.

The carbon monoxide can make up at least part (preferably at least 0.5 bar absolute) of the atmosphere above the solution in the crystallization or recrystallization reactor (or reactor headspace) or can create within the said reactor a pressure which is greater than the atmospheric pressure.

In practice, the process will therefore be operated under an absolute pressure of from 0 to 50 bars of carbon monoxide, the upper limit not being critical in nature but being representative of industrial apparatus which is not excessively expensive.

Preferably, the absolute pressure of carbon monoxide will be between 1 bar and 50 bars.

The crude adipic acid subjected to recrystallization according to the present process is usually an adipic acid which has already undergone one or more purification treatments, in particular by crystallization from water, by refining or else by distillation, to give it a minimum purity of approximately 95%.

Generally, the adipic acid recrystallized by the process of the invention has a purity of from 95 to 99.95%.

The recrystallization consists in taking the adipic acid to be purified and dissolving it in the minimum amount of hot water, i.e. usually at a temperature from 80 to 250° C., in the presence of a strong protic acid and/or under an at least partial pressure or atmosphere of carbon monoxide, and in then inducing crystallization of the dissolved adipic acid by cooling the solution, optionally after having seeded the solution using crystals of pure adipic acid.

Generally, the quantity of water employed is that which leads to a saturated solution of adipic acid at the chosen temperature. By way of indication, at 80° C. the saturated solution contains approximately 40% of adipic acid by weight per weight.

The process of the invention likewise embraces the crystallization of adipic acid from reaction mixtures in which it is present.

It is thus possible, for example, to crystallize adipic acid from the mixture obtained by hydroxycarbonylation of pentenoic acid with water and carbon monoxide. This reaction mixture can be mixed with the water in the presence of a strong protic acid and/or under an at least partial pressure or atmosphere of carbon monoxide, and the whole mixture can be kept at a temperature from 80 to 250° C. as indicated above for the recrystallization.

Since the promoter used in the hydroxycarbonylation reaction may be hydroiodic acid or hydrobromic acid, it may not be necessary to add the strong protic acid. However, if desired, the quantity of strong protic acid present in the reaction mixture may be supplemented.

Similarly, since the hydroxycarbonylation reaction is conducted in the presence of carbon monoxide, it may not be necessary to add this compound for the crystallization, although this possibility is not excluded if appropriate. As for the recrystallization of adipic acid, it is also possible to operate in the absence of carbon monoxide, by purging the atmosphere of the hydroxycarbonylation mixture prior to its crystallization.

The examples which follow illustrate the invention.

EXAMPLE 1

A glass bulb is charged with 5.16 g of adipic acid, containing 31.0 µg of Co (0.0006% by weight per weight of adipic acid), and 7.5 ml of water. The adipic acid has been prepared by direct oxidation of cyclohexane in the presence of Co acetate and has been purified by recrystallization from water. It does not contain any measurable quantities of organic impurities.

The open bulb is placed in a 125 ml autoclave, which is then closed.

The headspace is filled cold with carbon monoxide (approximately 1 bar).

The temperature is raised to 185° C. and is maintained at this level for approximately 30 minutes.

After cooling the autoclave and purging it with nitrogen, the adipic acid is filtered off and the autoclave is rinsed with a few ml of water.

The adipic acid filtered off is washed with 2 times 5 ml of water and then 3 times 8 ml of water.

The adipic acid is dried overnight in an oven (60° C.). The cobalt present in the final adipic acid is assayed by inductively coupled plasma in conjunction with mass spectrometry (ICP/mass). 0.000012% of Co by weight per weight is found.

EXAMPLE 2

Example 1 is repeated, charging 5.21 g of the same batch of adipic acid, containing 31.2 µg of Co (0.0006% by weight per weight of adipic acid), 7.5 ml of water and 1 ml of a solution of 96.7 mg of HCl in 50 ml of water. The molar ratio of HCl to Co is 10.

The operating conditions are the same as for Example 1 except that the CO headspace is replaced by a nitrogen headspace (1 bar absolute).

After washing and drying, the cobalt present in the final adipic acid is quantified. 0.00009% of Co by weight per weight is found.

EXAMPLES 3 TO 7

Example 1 is repeated with an adipic acid containing iridium. The adipic acid was prepared by hydroxycarbonylation of 3-pentenoic acid in the presence of a catalyst based on Ir and was purified by recrystallization from water. It contains no measurable quantities of organic impurities.

Table 1 below summarizes the conditions under which the examples were carried out (Tp=temperature) and the initial and final contents of Ir (initial Ir and final Ir), expressed in micrograms per gram, of the adipic acid (AdOH) employed.

TABLE 1

| Example | AdOH in g | Water in g | Tp in ° C. | Duration in min | CO in bars | Molar ratio HI:Ir | Initial Ir | Final Ir |
|---|---|---|---|---|---|---|---|---|
| Ex. 3 | 5.2 | 7.75 | 185 | 30 | 30 | 10 | 2.2 | 0.86 |
| Ex. 4 | 5.2 | 9.0 | 185 | 1200 | 1 | 10 | 2.2 | 0.82 |
| Ex. 5 | 5.35 | 8.2 | 185 | 1200 | 1 | 20 | 2.2 | 0.92 |
| Ex. 6 | 4.9 | 7.25 | 90 | 30 | 0(1 bar N2) | 10 | 5.0 | 3.8 |
| Ex. 7 | 4.95 | 8.0 | 185 | 1200 | 0(1 bar N2) | 20 | 2.2 | 1.06 |

EXAMPLE 8

A round-bottomed glass flask fitted at the top with a condenser and equipped with means for heating and cooling is charged with 5.44 g of adipic acid, containing 0.00095% of Rh, 7.5 g of water and an aqueous solution of HI (molar ratio of HI to Rh present in the adipic acid=10). The adipic acid was prepared by hydroxycarbonylation of 3-pentenoic acid in the presence of an Rh-based catalyst and was purified by recrystallization from water. It contains no measurable quantities of organic impurities.

A nitrogen headspace is established cold (1 bar approximately).

The reaction mixture is heated to 90° C. and this temperature is maintained for approximately 30 minutes.

After cooling, the adipic acid is filtered off and washed with 2 times 5 ml of water saturated in adipic acid.

The adipic acid is dried overnight in an oven (60° C.). The rhodium present in the final adipic acid is measured. 0.00054% of Rh by weight per weight is found.

Comparative Test 1

An adipic acid obtained by hydroxycarbonylation of 3-pentenoic acid in the presence of iridium and HI is recrystallized from water. This adipic acid has already undergone one crystallization and still contains 0.00022% of iridium.

The recrystallization is carried out conventionally by dissolving adipic acid in the minimum amount of water at approximately 95° C. and then by gradual cooling of the resulting solution, followed by filtration and, finally, by washing of the adipic acid filtered off with 2 times 5 ml of water and with 3 times 8 ml of water.

The adipic acid is dried overnight in an oven (60° C.). The iridium present in the final adipic acid is assayed. 0.00022% of Ir by weight per weight is found. Therefore, the iridium content of the adipic acid has not been successfully reduced.

What is claimed is:

1. A process for purifying adipic acid having a minimum purity of approximately 95% and containing traces of a catalyst, the process comprising the steps of:
   a) dissolving the adipic acid in the presence of at least one of a strong protic acid and carbon monoxide; and
   b) including crystallization of the dissolved adipic acid.

2. The process of claim 1, wherein the catalyst comprises at least one of iridium, rhodium, and cobalt.

3. The process of claim 1, wherein the strong protic acid has a pKa of less than 1.

4. The process of claim 1, wherein the strong protic acid comprises hydroiodic acid, hydrobromic acid, hydrochloric acid, nitric acid or sulphuric acid.

5. The process of claim 1, wherein the strong protic acid is present in a quantity ranging between 0 to 100 mol per mole of the catalyst.

6. The process of claim 5, wherein the quantity is between 1 and 50 mol per mole of catalyst.

7. The process of claim 1, wherein the carbon monoxide is present under an absolute pressure of 0 to 50 bars.

8. The process of claim 7, wherein the absolute pressure is between 1 to 50 bars.

9. The process of claim 1, further comprising seeding the solution of dissolved adipic acid with crystals of pure adipic acid.

10. The process of claim 1, wherein step a) comprises dissolving the adipic acid in purified water at a temperature of 80 to 250° C.

* * * * *